United States Patent [19]

Moore

[11] Patent Number: 5,451,218

[45] Date of Patent: Sep. 19, 1995

[54] URINARY DRAINAGE DEVICE

[76] Inventor: Patrick S. Moore, 90 MorningSide Dr., Apt. 3-J, New York, N.Y. 10027

[21] Appl. No.: 204,739

[22] Filed: Mar. 2, 1994

Related U.S. Application Data

[63] Continuation-in-part of Ser. No. 122,714, Sep. 15, 1993.

[51] Int. Cl.⁶ .............................................. A61M 1/00
[52] U.S. Cl. ..................................... 604/317; 604/349
[58] Field of Search ................ 604/73, 118, 119, 247, 604/96, 181, 134, 317, 318, 319, 349; 137/844; 417/472

[56] References Cited

U.S. PATENT DOCUMENTS

| | | | |
|---|---|---|---|
| 2,397,257 | 3/1946 | Goland et al. | 128/276 |
| 3,319,684 | 5/1967 | Calhoun | 150/8 |
| 3,672,372 | 6/1972 | Heimlich | 604/247 |
| 3,774,611 | 11/1973 | Tussey et al. | 128/278 |
| 3,800,795 | 4/1974 | Walker | 128/275 |
| 3,809,087 | 5/1974 | Lewis, Jr. | |
| 3,875,941 | 4/1975 | Adair | 128/278 |
| 4,141,361 | 2/1979 | Snyder | 128/278 |
| 4,227,533 | 10/1980 | Godfrey | 604/247 |
| 4,710,169 | 12/1987 | Christopher | 604/104 |
| 4,981,474 | 1/1991 | Bopp et al. | 604/133 |
| 5,019,059 | 5/1991 | Goldberg et al. | 604/317 |
| 5,300,033 | 4/1994 | Miller | 137/844 |

FOREIGN PATENT DOCUMENTS

348493  2/1922  Germany .............................. 604/349

*Primary Examiner*—Jerome L. Kruter
*Attorney, Agent, or Firm*—Greenlee and Winner

[57] ABSTRACT

The invention relates to an improved urinary drainage device which simulates the inlet end of the normal, non-catheterized urethra. This novel design significantly reduces the risk of urinary tract infection typically associated with internal catheters by providing a drainage duct comprising a truncated, collapsible inner lumen. Like the non-catheterized urethra, the collapsible inner lumen collapses after urination to prevent urine back flow. The invention further relates to an improved evacuator-type collection receptacle, the improvement comprising a resilient means or displacement means for controlling the negative pressure created within the collection receptacle.

5 Claims, 3 Drawing Sheets

URINARY DRAINAGE DEVICE

This application is a continuation-in-part of U.S. patent application Ser. No. 08/122,714, filed Sep. 15, 1993, now pending which is incorporated herein by reference.

FIELD OF THE INVENTION

The present invention relates generally to urinary drainage devices. More particularly, this invention relates to an apparatus for reducing the likelihood of urinary tract infection during continuous urine collection using a truncated, collapsible inner lumen and an evacuator-type collection receptacle.

BACKGROUND OF THE INVENTION

Various devices are known in the art for draining and collecting fluids from body cavities, including collection systems specifically designed for urinary bladder drainage. Most such urine collection devices are simple in design, consisting of a flexible catheter duct connected to a urine receptacle. The catheter duct is inserted through the urethra into the urinary bladder, and urine flows in small quantities as it is produced through the catheter into the receptacle. Unfortunately, these conventional drainage devices often become contaminated during use. Infection then ascends in a retrograde manner from the collection receptacle to the patient via the catheter duct. Conventional catheter designs also permit back flow of urine from the receptacle into the bladder, particularly when the catheter duct is elevated above the bladder. Moreover, the urine can remain stagnant for extended periods in the indwelling catheter of existing devices, where microorganisms quickly proliferate at body temperatures. Because the urethra cannot close with existing catheters, catheterized patients experience notoriously high rates of urinary tract infections.

Evacuator-type drainage devices have been designed to minimize the back flow of fluid from the receptacle. Examples include U.S. Pat. No. 2,397,257 (Goland et al.), U.S. Pat. No. 3,774,611 (Tussey et al.), U.S. Pat. No. 3,875,941 (Adair), U.S. Pat. No. 4,141,361 (Snyder), U.S. Pat. No. 4,981,474 (Bopp et al.), and U.S. Pat. No. 5,019,059 (Goldberg et al.), disclosing bellows-type collection receptacles which act as reservoirs for receiving and collecting the body fluids. These collapsible bellows-type receptacles collect fluid as they return to their original shape. As additional fluid is collected, the weight of the fluid expands the bellows container thereby creating additional partial vacuum to draw additional fluid into the receptacle. None of these devices, however, prevent microbial ingress from this stale fluid into the body cavity. Assuming the negative pressure is generally sufficient to withdraw fluid from the indwelling duct, the suction mechanism can fail during operation (e.g., during handling or emptying of the receptacle) causing retrograde leakage of contaminated fluid into the catheter duct. The potential for infection is further increased with evacuator-type drainage devices since these devices typically require periodic opening to purge fluid and resume the suction, thereby exposing the closed drainage system to the surrounding atmosphere. Finally, in addition to the increased risk of infection, the negative pressure generated within the expanding receptacle can readily exceed safe levels, causing injury to the urinary tract, particularly the urinary bladder epithelium. None of these prior devices provide a means to compensate for the increasing weight of collected fluid generated during continuous collection, thus maintaining the negative pressure within an acceptable range.

Other "improved" drainage devices employ check valves which are positioned between the catheter duct and fluid receptacle and are designed to minimize back flow of fluid from the receptacle. Most existing check valves consist of a rubber tube sealed in the inlet neck of the receptacle and projecting into the receptacle. The walls of the valves are normally collapsed to prevent reverse flow but open to permit the flow of fluid into the receptacle under pressure. Examples include U.S. Pat. No. 3,298,370 (Beatty) which discloses a shielded check valve to minimize accidental closures, U.S. Pat. No. 3,312,221 (Overment) which discloses an improved "flutter" valve, and U.S. Pat. No. 3,967,645 (Gregory) which discloses a rigid plastic valve having increased sensitivity to back pressure. Although drainage devices having check valves at the receptacle inlet may successfully minimize back flow of receptacle contents into the catheter duct, such devices are deficient in several respects. First, as with other prior art drainage devices, the catheter ducts often become contaminated during use, thus increasing the risk of urinary tract infection. The catheter duct provides an open passage for bacterial ingress into the urinary tract. Second, urine can remain stagnant for extended periods in the indwelling duct, where bacteria quickly proliferate. While these check valves may reduce back flow from the receptacle, they do not prevent back flow of contaminated urine from the duct into the bladder. Urinary tract infections are therefore common in patients using such drainage devices. Third, because the check valves in these devices are positioned at the distal end of the catheter duct, the valves themselves are susceptible to accidental closure from external pressure. Outside forces, including the patient or his clothing, may bear on the valve in such a way that flow into the receptacle is inhibited and back flow may occur because the valve is effectively held closed.

U.S. Pat. No. 3,800,795 (Walker) discloses another "improved" urinary drainage collecting device, the improvement comprising a leaf-type check valve at the receptacle inlet to prevent back flow and a complex ventilation system designed to minimize urine in the catheter duct. This design, however, suffers from the aforementioned disadvantages, namely those associated with an indwelling, non-collapsible catheter duct and an external check valve at the receptacle inlet.

U.S. Pat. No. 4,710,169 (Christopher) discloses yet another "improved" urinary drainage collecting device, the improvement comprising a segmented catheter wherein two relatively short semi-rigid segments are separated and joined together by a collapsible intermediate segment. The device is inserted using a plastic sound or probe which is removed and discarded after insertion.

A need therefore exists for a device for draining urine from incontinent patients which collapses after urination at the inlet end of the urethra to prevent urine back flow from the duct into the bladder. A need also exists for a device which minimizes the risk of back flow and retrograde infection from the fluid receptacle into the urinary tract, but which is safe and reliable in operation.

SUMMARY OF THE INVENTION

The present invention comprehends an improved urinary drainage device which, while being simple and economical in design, avoids the above-described problems associated with prior art devices.

More specifically, the present invention provides an improved urinary drainage device which simulates the proximal or inlet end of the normal, non-catheterized urethra. This novel design significantly reduces the risk of urinary tract infection typically associated with internal catheters by providing a truncated, collapsible inner lumen positioned at or near the proximal end of the drainage duct. Like the non-catheterized urethra, the inner lumen collapses after urination to prevent urine back flow and bacterial ingress from the drainage duct into the bladder. The truncated lumen is normally collapsed to prevent reverse flow into the bladder, but opens to permit the flow of urine into the duct under very slight pressure.

Still another principal aspect of this invention is to provide an improved urinary drainage device which minimizes retrograde infection and back flow of urine from the collection receptacle into the drainage duct using a safe and reliable suctioning means. The suctioning means as used herein comprises an evacuator-type collection receptacle, said collection receptacle comprising a resilient bellows container for receiving and collecting the urine. The bellows container is attached at the top to a rigid support frame, and connected at its base to the frame by slidable rings. The drainage device of the present invention further comprises a resilient means for initiating and ultimately stabilizing the partial vacuum within the collection receptacle. In a preferred embodiment, the resilient means is a spring or series of spring elements. In accordance with this aspect of the invention, the spring element(s) is attached at one end to the base of the bellows container and fixed at the other end to the rigid support frame. The spring element initially aids the collapsed bellows container to return to its uncollapsed state, whereby during its return to its uncollapsed state a partial vacuum is created within the container to draw fluid into the receptacle. As the bellows container expands with collected fluid, the spring is restored to its original unstretched condition. After the spring element has been restored to its original state, the restoring force of the spring acts to counterbalance the compressive force of urine in the receptacle, thus restricting the vacuum generated therein. The present invention thus provides a significant improvement over prior devices by providing a more consistent evacuation pressure within the collection receptacle.

Yet another aspect of the invention is to provide an improved urinary drainage device which minimizes the health risks associated with existing evacuation devices, namely damage to the urinary bladder epithelium, using a simple and reliable fluid displacement means. In accordance with this aspect of the invention, the drainage device comprises a suctioning means as described above, except that the resilient means is replaced with a fluid displacement means. Like the above-described resilient means, the displacement means stabilizes the partial vacuum created within the collection receptacle. In a preferred embodiment, the displacement means is a container partially filled with a fluid. The bellows receptacle is initially positioned above the surface of the fluid in the container, but it descends into the substance during continuous collection. After the receptacle has become suspended in the liquid, the weight of collected urine (and hence the negative pressure generated thereby) is offset by the buoyant force of the liquid. Thus, like the restoring force of a spring, the buoyant force of the liquid counterbalances the gravitational force of collected urine in the receptacle, thus stabilizing the vacuum generated therein.

The exact nature of this invention as well as other features and advantages thereof will be readily apparent from consideration of the specification, including the drawings. Those of skill in the art will appreciate that the invention described herein is susceptible to many modifications and variations without departing from its scope as defined by the appended claims.

BRIEF DESCRIPTION OF THE DRAWINGS

The accompanying drawings illustrate preferred embodiments of the invention, wherein.

DESCRIPTION OF THE PREFERRED EMBODIMENTS

Figure 1:
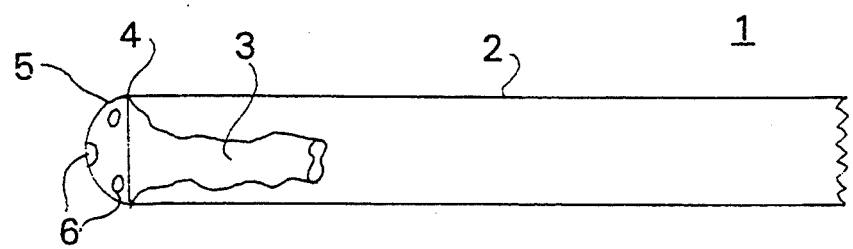
FIG. 1 is a sectional view of the urinary drainage device in an embodiment of the present invention.

Referring now to the drawings, like numbers indicate like features and the same number appearing in more than one figure refers to the same element.

Figure 2:
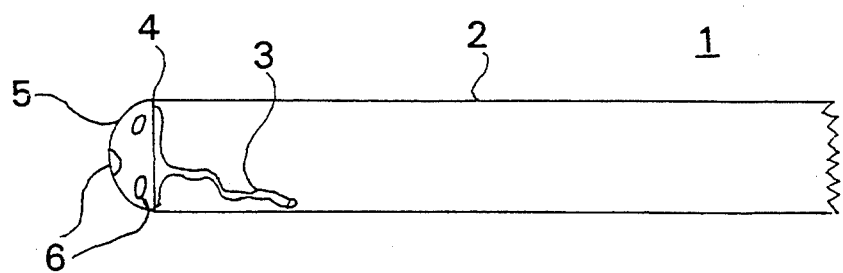
FIG. 2 is a view similar to FIG. 1, but illustrating the truncated, inner lumen in collapsed position.

FIGS. 1 and 2 illustrate a drainage duct 1 comprising a flexible outer tube 2 and a truncated, collapsible inner lumen 3 in the urinary drainage device of the present invention. The collapsible inner lumen 3 is attached at or near the proximal end 4 of the drainage duct 1. The collapsible inner lumen 3 is preferably 0.5 to 12 inches, and most preferably 1 to 6 inches in length. The truncated inner lumen 3 opens during bladder contractions to facilitate urine flow, as shown in FIG. 1, then collapses after urination to prevent back flow, as shown in FIG. 2. The collapsible inner lumen 3 thus simulates the proximal or inlet end of the normal, non-catheterized urethra, thereby eliminating the risk of retrograde infection commonly associated with urinary drainage devices.

The drainage duct 1 is a cylindrical tube having an inlet or proximal end 4 and a receptacle or distal end (not shown) removably connected to a fluid collection receptacle (not shown). The proximal end 4 terminates in a rounded head 5, said head preferably comprising multiple apertures 6 to reduce the risk of injury to the urinary bladder epithelium due to localized suction. The proximal end 4 of the drainage duct 1 further comprises an anchoring means (not shown), such as an expandable elastic collar, for anchoring the drainage device within the bladder. The anchoring means communicates with an inlet port (not shown) via an internal lumen (not shown) formed within the outer tube 2. The inlet port is removably connected to an inflating means (not shown) for inflating said elastic collar and anchoring said drainage duct 1 after insertion. The elastic collar is deflated prior to withdrawing the drainage device by attaching a suctioning means to the inlet port and creating a vacuum therein. The use of an expandable anchoring means is customary in the art, the construction and use of which is a matter of ordinary skill.

The outer tube 2 is formed of a flexible rubber latex or plastic biocompatible material, as is known in the art. The truncated, collapsible inner lumen 3 may be formed of any flexible polymeric non-toxic material. Preferably, the inner lumen 3 is made of a hydrophobic material or has an interior surface coating of a hydrophobic substance such as a silicone. The hydrophobic material or inner coating minimizes residual urine retention which might otherwise occur as a thin film between the collapsed walls of inner lumen 3. Some degree of self-adherence of the inner surface of inner lumen 3 is desirable to maintain a collapsed state in the absence of urine flow and to prevent retention of a film of urine between the collapsed inner walls. However, the self-adherence must not be so strong as to prevent separation of the collapsed lumen walls under urinary bladder pressure when the patient needs to empty his or her bladder. The selection and optimization of operative materials and coatings is a matter of ordinary skill in the art.

Figure 4:
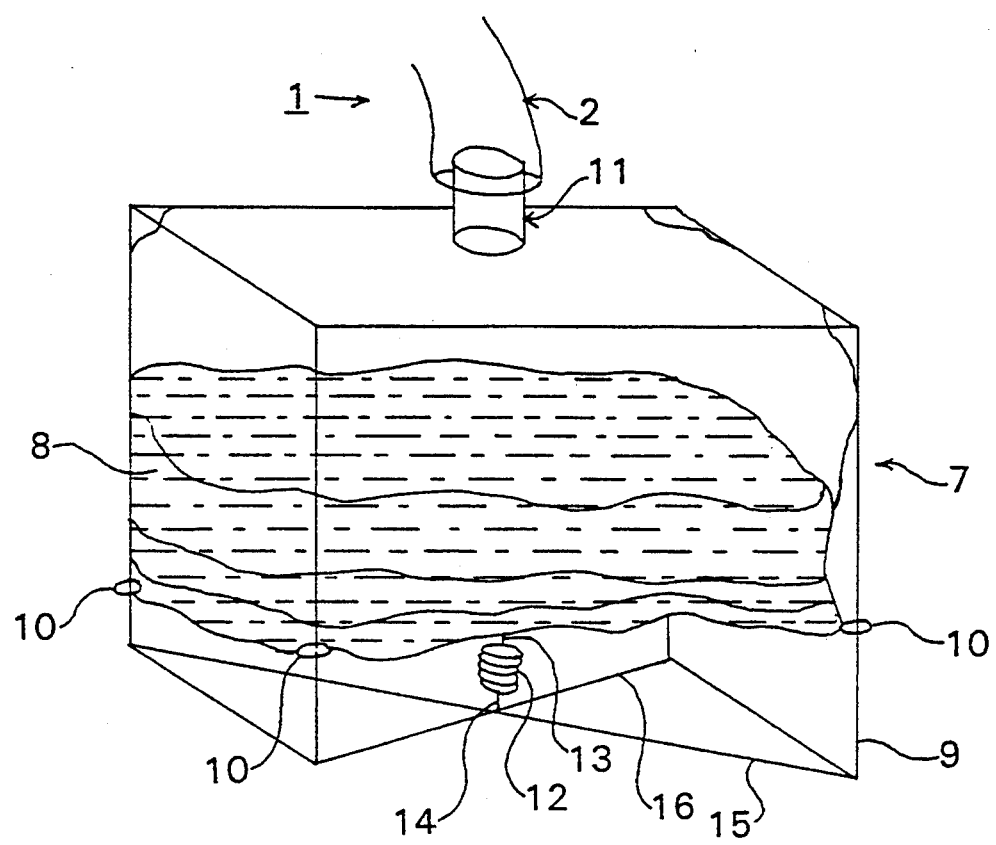
FIG. 4 is a perspective view of the evacuating receptacle in an embodiment of the present invention, showing the receptacle and spring element in their partially expanded and compressed conditions, respectively.

In an alternate preferred embodiment (not shown), the inlet or proximal end 4 of the drainage duct 1 has a collapsible neck comprising an elastic ring. The elastic ring expands during urination to facilitate urine flow, then collapses under normal pressure to prevent urine back flow. This alternate embodiment further comprises an anchoring means at the proximal end 4, such as the expandable elastic collar described above in regard to FIGS. 1 and 2. This alternate preferred embodiment is illustrated in FIGS. 4 through 6 of copending U.S. patent application Ser. No. 08/122,714, which is incorporated herein by reference.

Figure 3:
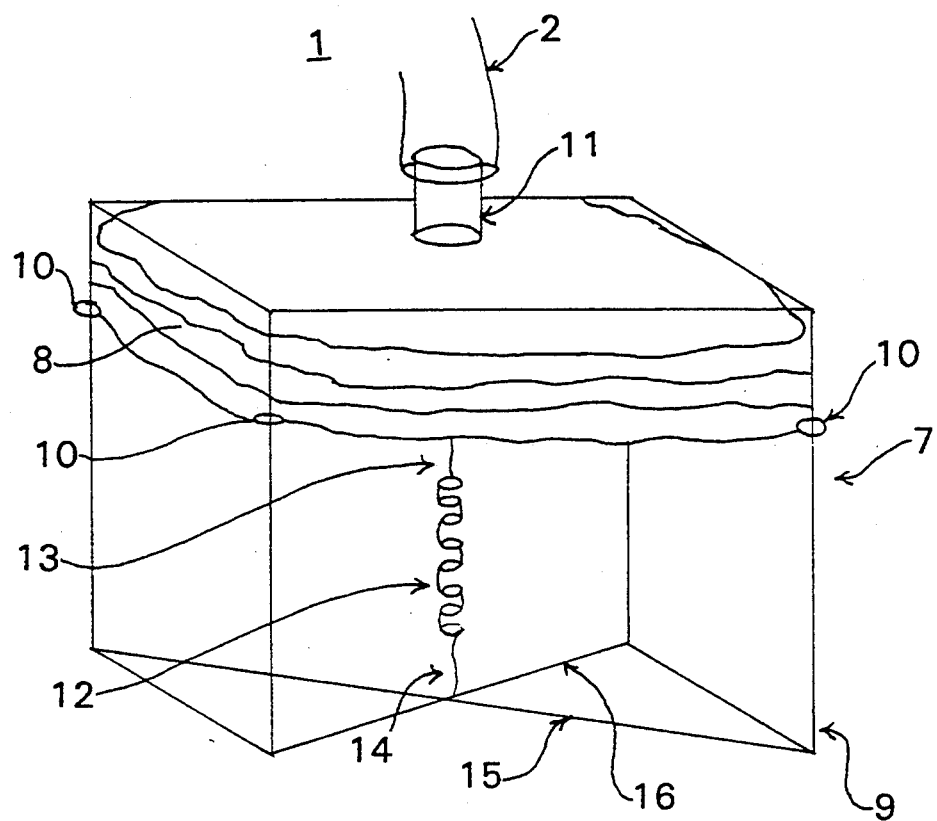
FIG. 3 is a perspective view of the evacuating receptacle in an embodiment of the present invention, showing the empty receptacle and spring element in their collapsed and extended conditions, respectively.

FIGS. 3 and 4 illustrate the evacuator-type collection receptacle 7 in the urinary drainage device of the present invention. In the present form of the invention, the evacuator-type collection receptacle 7 comprises a bellows-type collapsible container 8 for receiving and collecting the urine. The bellows-type container 8 is preferably constructed of polyethylene or polypropylene, although it may be made of other impervious resilient materials. In fact, the suctioning may be accomplished using any container capable of producing sufficient negative pressure during evacuation to draw the urine from the drainage duct 1. The bellows container 8 is attached at the top to a rigid support frame 9. The bellows container 8 is further connected to the support frame 9 at its base through suitable sliding means, such as the ring connectors 10 shown in the figures. The collected urine enters the bellows container 8 through a tube connector 11 to which the drainage duct 1 is attached.

In the preferred embodiment shown in FIGS. 3 and 4, a spring element 12 is attached to the base of the collapsible container 8. The spring element 12 facilitates the initiation and ultimately the stabilization of the partial vacuum created within the bellows container 8. The spring element 12 is attached at a first end 13 to the base of the bellows container 8 and fixed at a second end 14 to a suitable support means. The suitable support means can be any fixed structure including, but not limited to, the support frame 9 or a structure associated therewith. In the embodiment illustrated in FIGS. 3 and 4, the support means comprises a pair of interconnected crossbars 15 and 16 formed at the base of the rigid support frame 9.

The spring element 12 is preferably mounted under a force of sufficient magnitude to cause the spring to stretch (FIG. 3), thereby storing sufficient energy to generate a preselected range of initial vacuum pressure within the bellows container 8. This range can be varied by spring selection to accommodate a variety of vacuum pressure needs.

As the bellows container 8 collects urine, the spring element 12 is restored to its original unstretched condition. After the spring element 12 attains its original state, it then acts to counterbalance the compressive force of collected urine in the bellows container 8, thereby restricting the vacuum generated therein (FIG. 4). By varying the size and spring index or stiffness coefficient of the spring element 12, the vacuum generated within the bellows container 8 can be maintained within preselected values. Such optimization is well within the skill of the ordinary artisan. The present invention thus provides a significant improvement over prior devices by providing a controlled evacuation pressure.

In an alternate embodiment (not shown), the evacuation pressure is controlled using a fluid displacement means. Like the resilient means (exemplified herein by the spring element 12), the displacement means stabilizes the partial vacuum created within the bellows container 12. In a preferred embodiment, the displacement means is an opened container partially filled with a fluid substance, preferably water. The bellows container 12 is initially positioned above the fluid in the partially filled container. As the bellows container 12 expands with collected urine, it descends into the underlying substance. Once the bellows container 12 is suspended in the fluid, the buoyant force of the fluid acts to counterbalance the gravitational force of collected urine in the bellows container 8, thereby restricting the vacuum generated therein.

Obviously, many modifications and variations of the present invention are possible and will be evident to those of ordinary skill in the art. For example, the improved urinary drainage device can incorporate one or all of the various embodiments described herein, namely a drainage duct comprising a truncated, collapsible inner lumen in combination with a modified evacuator-type collection receptacle. Each of these embodiments may be used individually or in combination to improve existing drainage devices. Moreover, although the exemplified resilient means comprises a single helical-coil compression spring, the invention contemplates all types of resilient means including, but not limited to, conical coil springs, extension springs, torsion springs, leaf springs and disc springs, either individually, in series, or in combination. It is therefore to be understood that within the scope of the appended claims, the invention may be practiced in ways other than as specifically described herein.

I claim:

1. A urinary drainage device comprising:
   a tube for draining urine from a patient, said tube comprising a flexible outer tube and a truncated, collapsible inner lumen;
   a suctioning means connected to said tube for suctioning and receiving urine, wherein said suctioning means comprises a resilient container which is compressible to create a suctioning force as it returns to its normal expanded condition, and wherein said resilient container has a top portion attached to a rigid support frame and a bottom portion slidably connected to said support frame; and a means to stabilize the suctioning force created within said resilient container, wherein said stabilizing means comprises at least one spring element, and wherein said spring element has a first end attached to the resilient container and a second end attached to a support means, wherein said support means comprises the rigid support frame.

2. The urinary drainage device of claim 1 wherein said spring element is a helical coil compression spring.

3. The urinary drainage device of claim 1 wherein said stabilizing means is a fluid displacement system.

4. The urinary drainage device of claim 3 wherein fluid displacement system is a container partially filled with a liquid, and wherein said container is positioned below said resilient container.

5. The urinary drainage device of claim 4 wherein said liquid is water.

* * * * *